US00PP31210P2

(12) United States Plant Patent
Petersen

(10) Patent No.: US PP31,210 P2
(45) Date of Patent: Dec. 10, 2019

(54) ***ALLIUM* PLANT NAMED 'ERIPET06'**

(50) Latin Name: ***Allium* hybrid**
Varietal Denomination: EriPet06

(71) Applicant: Erik Petersen, Medford, OR (US)

(72) Inventor: Erik Petersen, Medford, OR (US)

( * ) Notice: Subject to any disclaimer, the term of this patent is extended or adjusted under 35 U.S.C. 154(b) by 0 days.

(21) Appl. No.: 16/350,508

(22) Filed: Nov. 26, 2018

(51) Int. Cl.
*A01H 5/02* (2018.01)
*A01H 6/04* (2018.01)

(52) U.S. Cl.
USPC ..... Plt./263.1
CPC ..... *A01H 6/04* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Allium* plant named 'EriPet06' that is characterized by its exhibits foliage with intense powdery blue foliage as the plant emerges in spring and changes to glaucous blue in summer, and its round rose-purple umbels in mid-summer.

2 Drawing Sheets

Botanical classification: *Allium* hybrid.
Variety denomination: 'EriPet06'.

BACKGROUND OF THE INVENTION

The present invention relates to a new and distinct cultivar of *Allium* plant, botanically of hybrid origin and will be referred to hereafter by its cultivar name, 'EriPet06'. 'EriPet06' represents a new cultivar of *Allium*, as a hardy herbaceous perennial grown for use as a landscape and container plant.

'EriPet06' was discovered by the Inventor in May of 2016 as a naturally occurring mutation of *Allium* 'Millenium' (not patented) that was growing in a container in a nursery block planted with bare-root divisions of 'Millenium' in Central Point, Oreg.

Asexual propagation of the new cultivar was first accomplished by the Inventor by division in spring of 2017 in Central Point, Oreg. Asexual propagation by division has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'EriPet06' as a unique cultivar of *Allium*.

1. 'EriPet06' exhibits foliage with intense powdery blue foliage as the plant emerges in spring and changes to glaucous blue in summer
2. 'EriPet06' exhibits round rose-purple umbels in mid-summer.

The parent plant of 'EriPet06', 'Millenium', differs from 'EriPet06' in having foliage that is green in color with a shiny surface. 'EriPet06' can also be compared to the *Allium senescens* cultivar 'Blue Eddy' (not patented) and *Allium* 'Medusa' (U.S. Plant Pat. No. 28,701). Both 'Blue Eddy' and 'Medusa' are similar to 'EriPet06' in having glaucous foliage. 'Blue Eddy' differs from 'EriPet06' in having twisted foliage and in flowering in late summer to early fall. 'Medusa' differs from 'EriPet06' in having foliage that is twisted and less blue in color.

BRIEF DESCRIPTION OF THE DRAWINGS

The accompanying colored photographs illustrate the overall appearance and distinct characteristics of the new *Allium*. The photographs were taken of plants of 'EriPet06' as grown in Central Point, Oreg.

The photograph in FIG. 1 was taken of a plant 1 year in age as grown outdoors and provides a view of the summer foliage of 'EriPet06' at the end of bloom.

Figure 1:
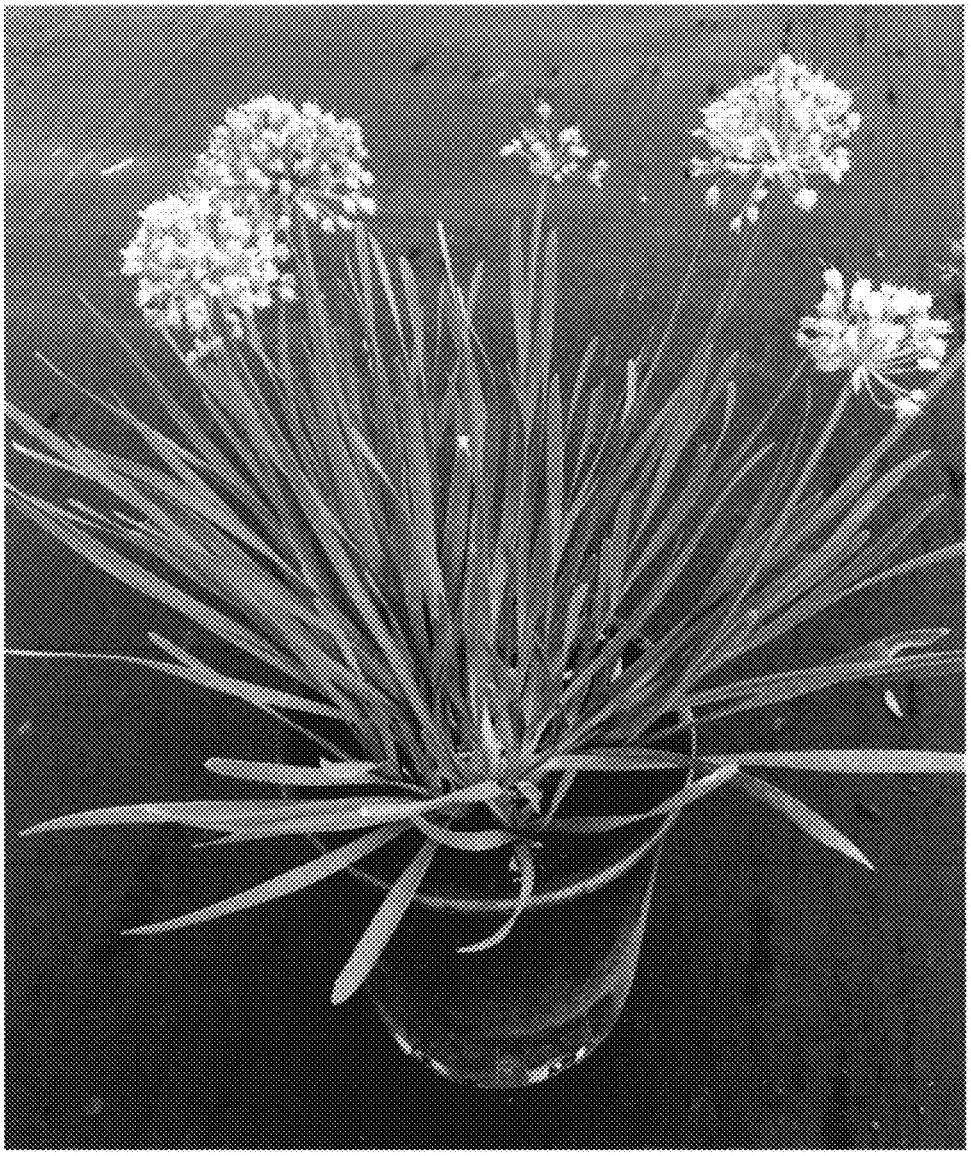
Figure 2:
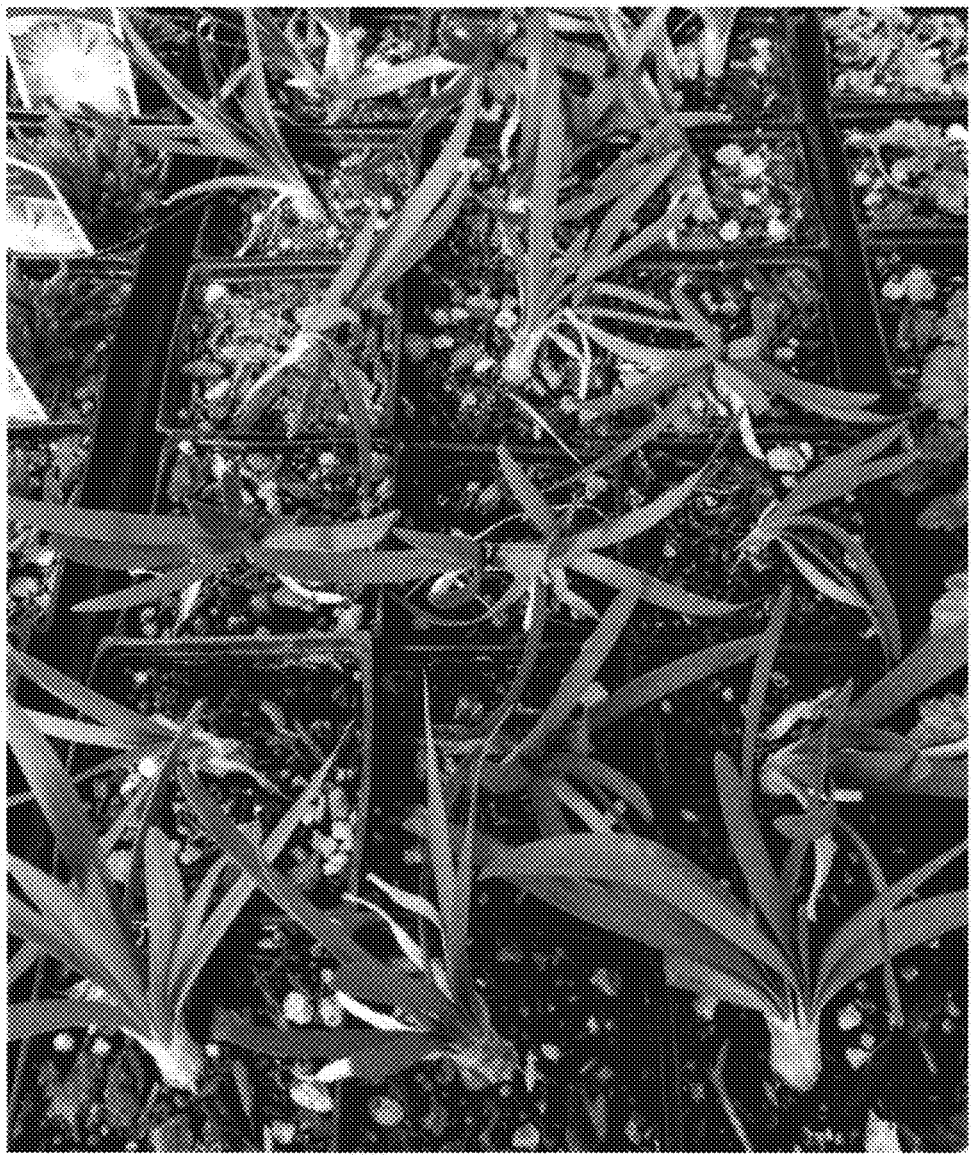

The photograph in FIG. 2 was taken of single divisions grown in 4-inch containers in the greenhouse provides a close-up view of the foliage in spring of 'EriPet06'.

The colors in the photographs may differ slightly from the color values cited in the detailed botanical description, which accurately describe the colors of the new *Allium*.

DETAILED BOTANICAL DESCRIPTION

The following is a detailed description of the new cultivar as observed for 1-year-old plants of 'EriPet06' as grown in 2-gallon containers in Central Point, Oreg. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming habit.*—Up to 4 weeks in mid-summer in Oregon.

*Plant type.*—Herbaceous perennial.

*Plant habit.*—Bulb with a tightly clump forming, compact and vase-shaped habit.

*Height and spread.*—An average of 42 cm in height in bloom, 40 cm in width.

*Hardiness.*—At least in U.S.D.A. Zones 4 to 9.

*Diseases and pests.*—No unique aspects concerning susceptibility or resistance to diseases or pests has been observed.

*Root description.*—Fibrous from base of bulbs.

*Branching.*—Stem-less, tufted shoots arise from bulbs.

*Bulb description.*—Oval-conical in shape, an average of 3 cm in length and 2 cm in width, glossy and smooth, roots are fibrous and thick, NN155D in color.

*Root development.*—10 to 12 weeks to multiply from one bulb to 12 to 13 bulbs.

*Propagation.*—Division.

*Growth rate.*—Vigorous, similar to other *Alliums*.

Foliage description:

*Leaf shape.*—Linear.

*Leaf division.*—Simple.

*Leaf base.*—Truncate to bulb.

*Leaf apex.*—Acute.

*Leaf aspect.*—Primarily upright.

*Leaf venation.*—Parallel, not prominent or conspicuous, color matches leaf color.

*Leaf margins.*—Entire.

*Leaf fragrance.*—Onion scented.

*Leaf attachment and arrangement.*—Sessile, arise in tufts from bulb.

*Leaf substance.*—Semi-succulent.

*Leaf size.*—24 cm in length, 8 mm in width.

*Leaf surface.*—Glabrous and dull to slightly glossy on upper and lower surface.

*Leaf color.*—Young; 145A, mature; NN137A, base 145B to 145C.

Flower description:

*Inflorescence type.*—Terminal umbel.

*Lastingness of inflorescence.*—Up to 4 weeks.

*Inflorescence size.*—An average of 6 cm in depth and 5 cm in diameter.

*Inflorescence quantity.*—Average of 6 per plant, 1 per stem.

*Flower fragrance.*—Onion scented.

*Flower number.*—Average of 90 per inflorescence.

*Flower aspect.*—Upright.

*Flower bud.*—An average of 6 mm in length, 3 mm in diameter, slightly glossy surface, oblong in shape, a blend of 76C to 76D and 77A in color.

*Flower form.*—Campanulate.

*Flower size.*—An average of 1 cm in depth, 8 mm in diameter.

*Tepals.*—6, ovate in shape, 8 mm in length, 3 mm in width, apex acute, base rounded, entire margins, inner and outer surface color when opening and mature; 76B, center vein 77A, fading to N75A, both surfaces glabrous and slightly glossy.

*Peduncles* (*flower stem*).—Oval in shape, strong, an average of 38 cm in length and 4 mm in width, held upright, glabrous and dull surface, NN137A in color.

*Pedicels.*—Round in shape, an average of 2 cm in length and 1 mm in width, glabrous and slightly glossy surface, 144A in color.

Reproductive organs:

*Gynoecium.*—Pistil; 1, 5 mm in length, stigmas; minute, 0.5 mm in length, NN155D in color, styles; 4 mm in length, N82A in color, ovary; tri-shaped, rounded, superior, NN155D in color, 3 mm in diameter.

*Androecium.*—Stamens; Average of 6, occasionally 7, 1 mm in length, filaments; 8 mm in length, 0.5 mm in width, glossy surface, color at base NN155D blending upward and becoming N82A, anthers; club shaped, 1 mm in length, 163A in color, pollen; low in quantity and 160A in color.

*Fruit and seed.*—None observed to date.

It is claimed:

1. A new and distinct variety of *Allium* plant named 'EriPet06' as described and illustrated herein.

* * * * *